United States Patent
Srouji

(12) 
(10) Patent No.: US 6,702,746 B1
(45) Date of Patent: Mar. 9, 2004

(54) ALVEOLAR BONE MEASUREMENT SYSTEM

(75) Inventor: Samer M. Srouji, Nazeret (IL)

(73) Assignee: Dentosonic Ltd., Nesher (IL)

( * ) Notice: Subject to any disclaimer, the term of this patent is extended or adjusted under 35 U.S.C. 154(b) by 0 days.

(21) Appl. No.: 10/018,886

(22) PCT Filed: Jun. 8, 2000

(86) PCT No.: PCT/IL00/00341
§ 371 (c)(1),
(2), (4) Date: Apr. 15, 2002

(87) PCT Pub. No.: WO01/00102
PCT Pub. Date: Jan. 4, 2001

(30) Foreign Application Priority Data

Jun. 23, 1999 (IL) .................................................. 130618

(51) Int. Cl.[7] .................................................. A61B 8/02
(52) U.S. Cl. .................................................. 600/449
(58) Field of Search .................. 600/407, 424–437, 600/438, 439, 440–447, 459, 449; 73/625, 626; 367/7, 11; 433/29, 72; 351/511

(56) References Cited

U.S. PATENT DOCUMENTS

| 3,890,959 A | * | 6/1975 | Youdin et al. ............. 600/431 |
| 4,169,984 A | | 10/1979 | Parisi |
| 4,828,052 A | | 5/1989 | Duran et al. |
| 4,838,853 A | | 6/1989 | Parisi |
| 4,913,157 A | * | 4/1990 | Pratt et al. .................. 600/449 |
| 4,941,474 A | * | 7/1990 | Pratt, Jr. ..................... 600/437 |
| 5,100,318 A | * | 3/1992 | Demyun et al. ............. 433/72 |
| 5,328,365 A | * | 7/1994 | Jacoby ......................... 433/29 |
| 5,427,105 A | | 6/1995 | Knapp et al. |
| 5,570,182 A | * | 10/1996 | Nathel et al. ................ 356/511 |
| 6,007,333 A | * | 12/1999 | Callan et al. ................. 433/29 |

FOREIGN PATENT DOCUMENTS

DE  42 05 360  8/1993

* cited by examiner

*Primary Examiner*—Ali M. Imam
(74) *Attorney, Agent, or Firm*—Browdy and Neimark

(57) ABSTRACT

An ultrasound system for assessment of distance between an area of interest and a known location of a non-bone canal for use in drilling in an implant receiving cavity in the alveolar bone of a human subject's posterior mandible or posterior maxilla. The system comprises an ultrasound probe capable of being introduced at the area of interest and transceiving pulse echo ultrasound signal to the alveolar bone and therefrom and an electronic circuitry for processing the ultrasound signal and providing an indication of the remaining alveolar bone distance between said ultrasound probe and a canal within the alveolar bone.

11 Claims, 3 Drawing Sheets

ALVEOLAR BONE MEASUREMENT SYSTEM

REFERENCE TO RELATED APPLICATIONS

The present application is the national stage under 35 U.S.C. 371 of international application PCT/IL00/00341, filed Jun. 8, 2000 which designated the United States, and which international application was published under PCT Article 21(2) in the English language.

FIELD OF THE INVENTION

This invention is in the field of alveolar bone measurement for the drilling of an implant receiving cavity for tooth replacement purposes. In particular the invention is concerned with aiding in determining the drilling depth of the implant receiving cavity in the alveolar bone.

BACKGROUND OF THE INVENTION

Endosseous osseointegrated, root form implants are employed for tooth replacement in both the posterior mandible and the posterior maxilla. Before commencing drilling of an implant receiving cavity, an investigation is made to determine the length of the longest physiologically possible implant which can be safely implanted whilst leaving sufficient alveolar bone tissue of about 2 mm either above the superior border of the mandibular canal in a posterior mandible, or below the inferior surface of the maxillary sinus in a posterior maxilla, through which the plexus of nerves extends. Hereinafter in the specification and claims, the term canal refers to the mandibular canal and to the posterior maxilla. Being more practical, it denotes a non-bone tissue within the posterior mandible and the posterior maxilla, respectively.

Such investigations are typically performed by way of panoramic X-ray radiography technique or, more occasionally, CT dental scans. To avoid possible puncturing of either a mandibular canal or a maxillary sinus, shorter implants than physiologically safe are typically employed which reduces osseointegration, with surrounding bone tissue thereby militating against successful implantation.

It is also of significance that the condition of the posterior mandible and the posterior maxilla be assessed prior to drilling an implant receiving cavity, in order to determine whether the bone is suitable for receiving an implant and to avoid unnecessary surgical performance. Such assessment may be carried out by examining the porosity of the bone tissue.

Thus, it is an object of the present invention to provide a method and a system for assessing the condition of a bone tissue, prior to drilling in the alveolar bone, and for assessing the depth remaining between an end wall of an implant receiving cavity and a non-bone tissue, namely a canal within the alveolar bone.

The term area of interest as used in the specification and claims, is used to denote the location at which a ultrasound probe is located, either over skin tissue, or on the bone surface (prior to drilling) or within a bore of the implant receiving cavity.

SUMMARY OF THE INVENTION

In accordance with the present invention, there is provided an ultrasound system for assessment of distance between an area of interest and a known location of a non-bone canal for use in drilling an implant receiving cavity in the alveolar bone of a human subject's posterior mandible or posterior maxilla, the system comprising:

(a) an ultrasound probe capable of being introduced at the area of interest and transceiving pulse echo ultrasound signal to the alveolar bone and therefrom; and (b) an electronic circuitry for processing the ultrasound signal, for providing an indication of the remaining alveolar bone distance between said ultrasound probe and a canal within the alveolar bone.

The present invention enables intraoperative determination of the length of the longest endosseous osseointegrated root form implant which can be safely implanted, thereby facilitating a more accurate procedure rather than hitherto available. The indication can be either an actual alveolar bone distance measurement, whereupon an implant receiving cavity can be further deepened until a recognized minimum thickness of alveolar bone remains. Alternatively, a warning indication can be provided when a predetermined minimum alveolar bone distance is reached whereupon the drilling of an implant receiving cavity is terminated. Either technique is suitable for tooth replacement in either a posterior mandible or a posterior maxilla.

The system of the present invention is useful also in accessing the condition (quality) of the alveolar bone, namely if performing an implant receiving cavity may be considered in light of the bones condition. This may be carried out prior to drilling by inserting the probe over either over skin tissue or on the bone surface prior to drilling and performing the procedure of steps (a) and (b) above.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
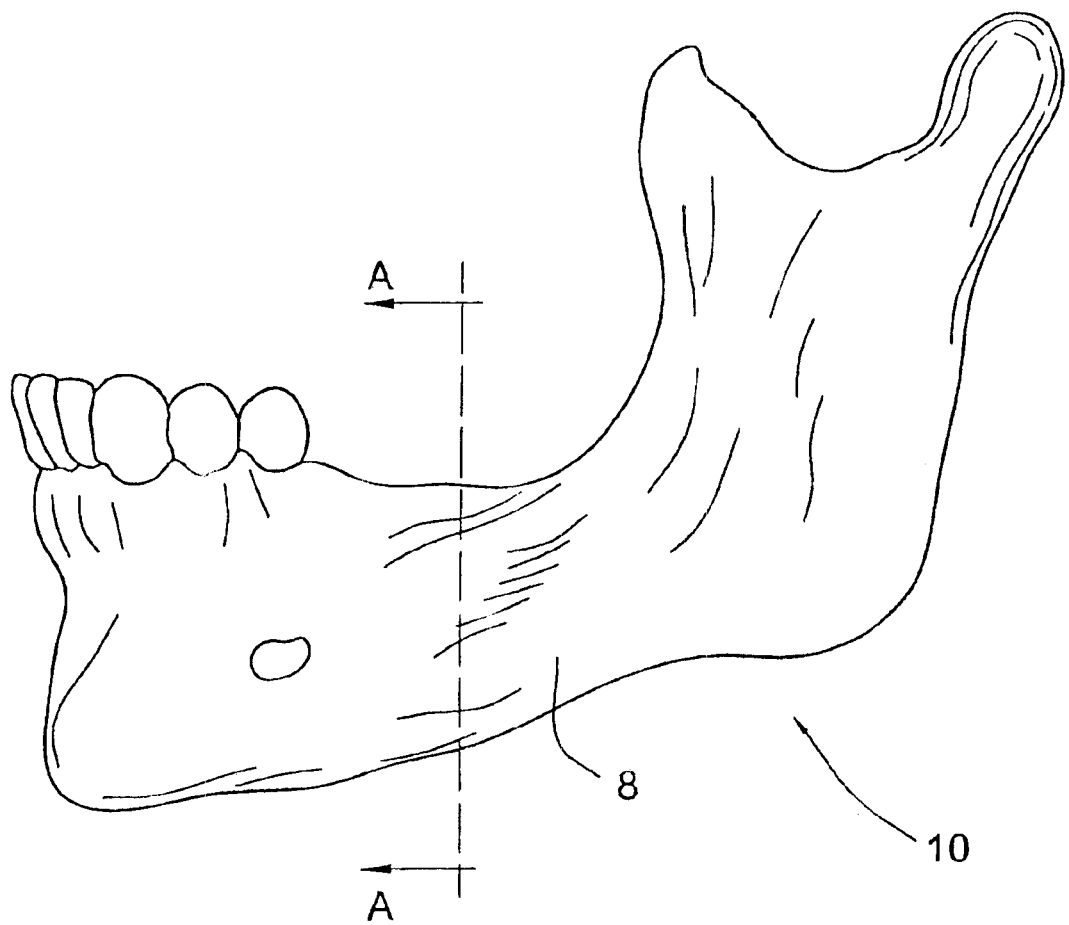
FIG. 1 is a perspective view of the posterior mandible of a human subject's lower jaw, on which a dental surgical procedure is to be performed.
Figure 2:
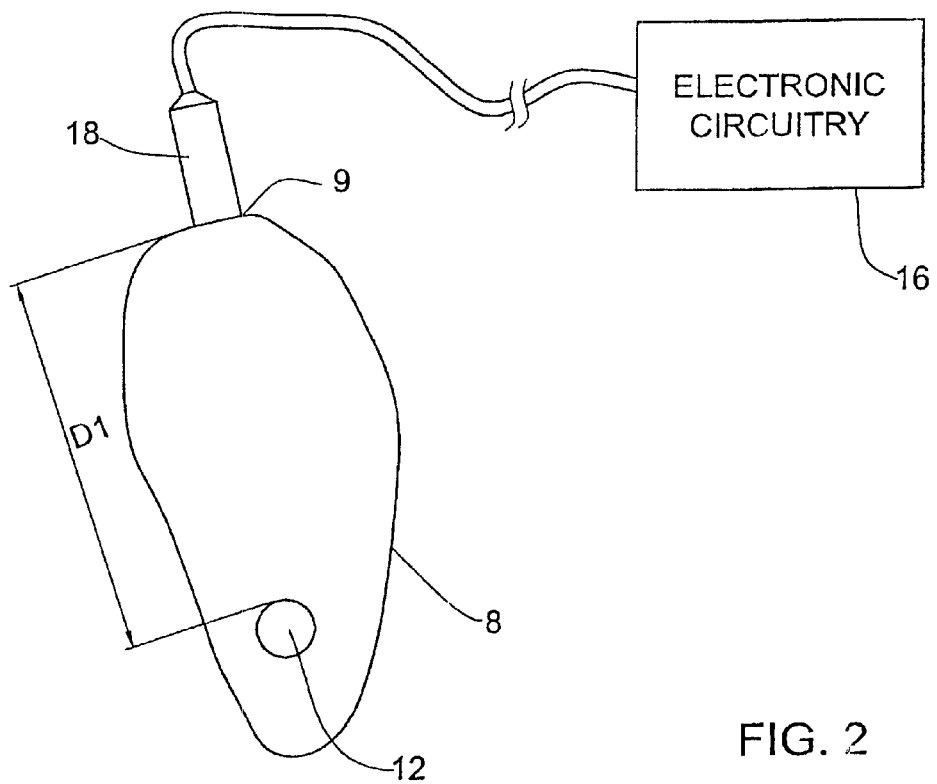
FIG. 2 is a representation of a system according to the invention, in a first mode of operation, before drilling in a transverse cross section cut along the line A—A in its perspective view shown in FIG. 1.
Figure 4:
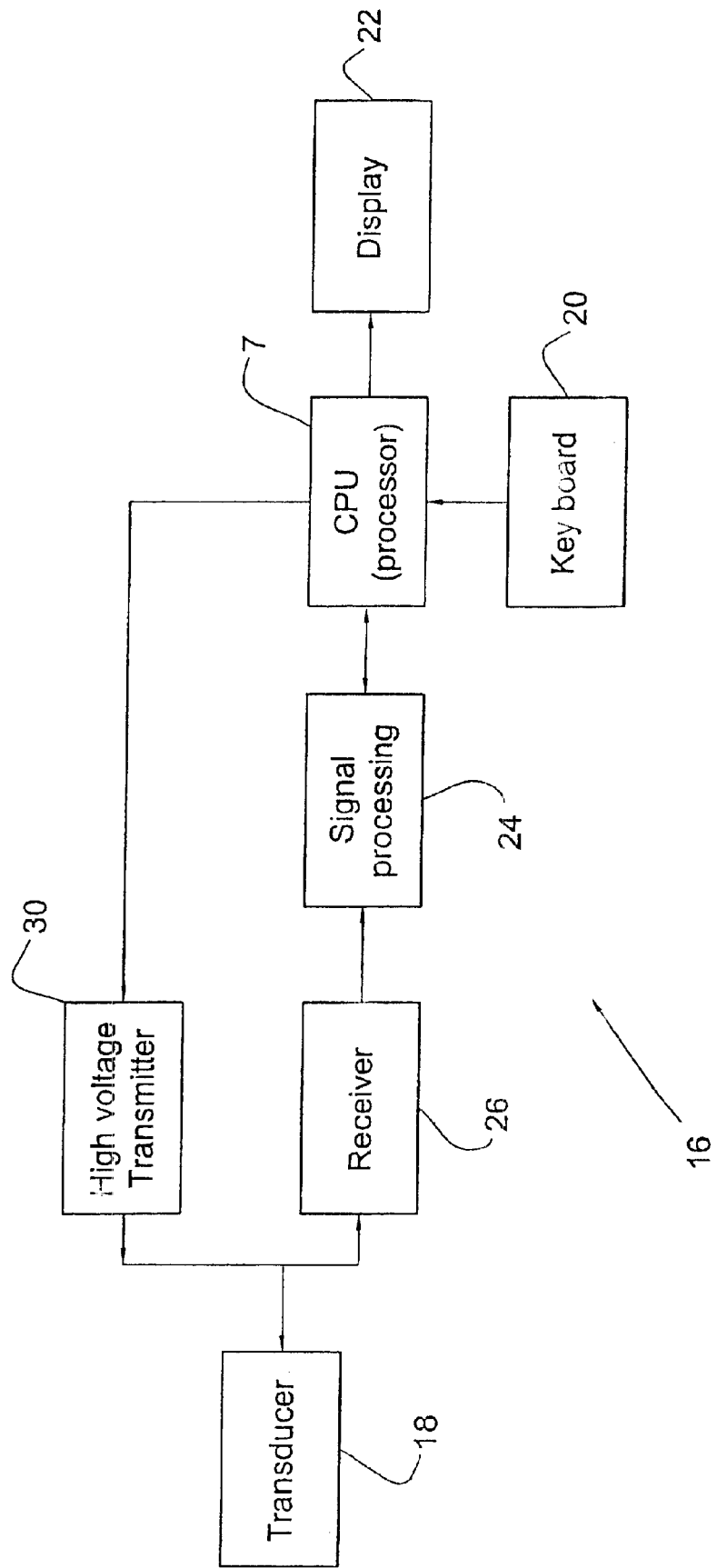
FIG. 4 is a block diagram of a system according to the present invention.

In FIG. 1 there is presented posterior mandible 8 of a human subject's lower jaw 10. In FIG. 2, an ultrasound system comprises an ultrasound probe (transducer) 18 which, in the present embodiment, is fitted for placing over a skin tissue (not shown) or directly over an exposed portion 9 of the bone, prior to drilling in the posterior mandible 8. Transducer 18 communicates with an electronic circuitry generally designated 16 which as can be seen in FIG. 4 comprises a processor 7 with a user interface 20 (typically a keyboard) and a display 22. The system further comprises a signal processing unit 24, a receiver 26 and a transmitter 30.

According to the procedure represented by FIG. 1, the probe (transducer) 18 is placed either on a skin tissue of the unexposed bone or over the exposed bone, as illustrated in the figure. Then an ultrasound signal is transmitted and the time of flight $T_{D1}$ of the ultrasound wave between the probes location (area of interest) and the superior surface of the mandibular canal 12 (i.e. the beginning of the non-bone tissue) is measured. The distance $D_1$ is proportional to the time of flight $T_{D1}$ and is determined by the processor, by multiplying the time of flight by the average velocity $V_{bone}$ of ultrasound within a bone tissue, as known per se.

When the transducer is placed on the overlaying soft skin tissue (not shown), a suitable calculation will then take into consideration its thickness, which can be derived out of the travel time $T_{D0}$ of the ultrasound wave through a first non-bone tissue $D_0$ (not shown). The information received from the time of flight will also provide information regarding the condition of the bone e.g. location of the mandibular canal 12 within the mandible, bone porosity, bone density, etc.

Figure 3:
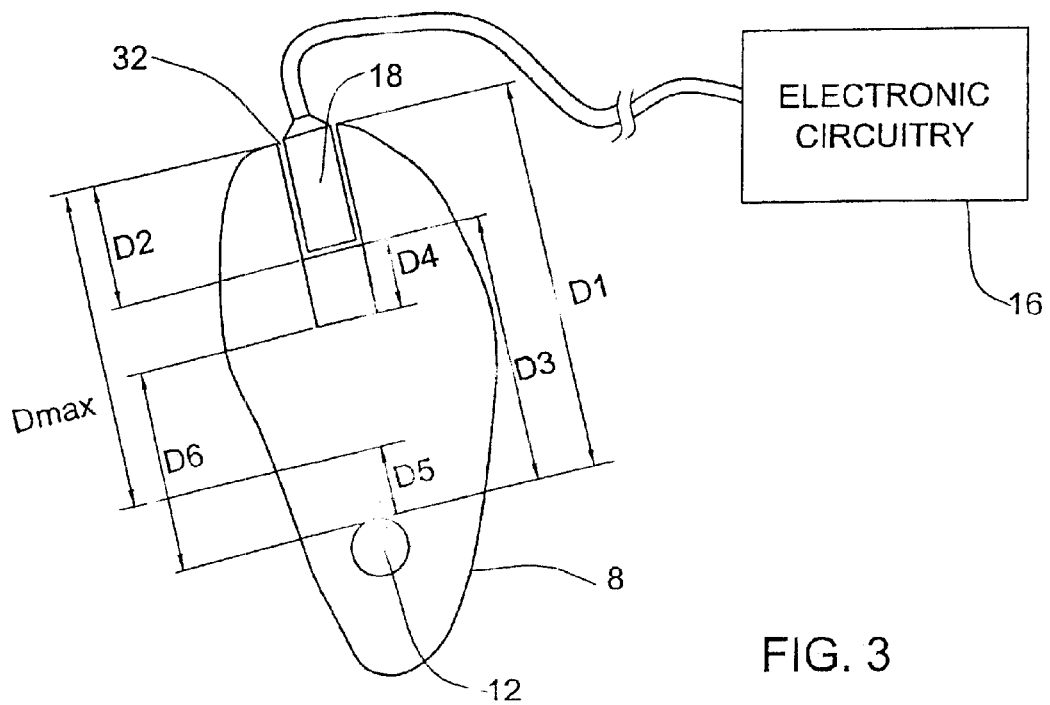
FIG. 3 is a representation of an ultrasound system for use in the drilling of an implant receiving cavity in the left posterior mandible of a human subject's lower jaw shown in a transverse cross section cut along the line A—A in its perspective view shown in FIG. 1.

An improved method for measuring the distance between an area of interest and the canal 12 is illustrated in FIG. 3, wherein the actual velocity $V_{boneact}$ of ultrasound within a bone tissue is calculated by first drilling a bore 32 of known depth $D_2$, and measuring the time of flight $T_{D3}$ of the ultrasound wave between the probes location within the bore 32 (area of interest) and the superior surface of the mandibular canal 12, from which distance $D_3$ can be derived as explained hereinabove.

Then, the depth of bore is increased by a measured distance $D_4$ represented by a dashed line (possibly to the required depth to serve in its capacity as an implant receiving cavity), and a second measurement of time of flight $T_{D6}$ takes place, so as to determine the distance $D_6$, as explained herein above. The actual velocity $V_{boneact}$ may than be derived out of the following equation:

$$V_{boneact} = D_4/(T_{D3} - T_{D6})$$

$V_{boneact}$ will also provide valuable information regarding the mechanical strength of the bone, by comparing the value $V_{boneact}$ to the norms of healthy subjects of the same age group, sex and ethnic origin.

This formula assumes that the time of flight within bone section $D_4$ is similar to that as in section $D_3$.

Having defined $V_{boneact}$, it is now possible to calculate the exact distance, as follows:

$$D_3 = T_{D3} * V_{boneact}$$

and the overall distance D1 between the surface of the bone (area of interest) and the superior surface of the mandibular canal 12 is calculated by the formula:

$$D_1 = D_3 + D_2$$

whereby a maximum safe depth $D_{max}$ of an implant receiving cavity would be calculated as:

$$D_{max} = D_1 - D_5$$

where $D_5$ is a minimal safety distance maintained from the superior surface of the mandibular canal. The value of this distance may change depending on different parameters and may be selected by the operator.

The use of the ultrasound system is now described for assessing the permissible depth for drilling an implant receiving cavity in a posterior mandible: A patient is anaesthetized and the site of the posterior mandible where the implantation is to take place is exposed. The exact location of the implantation is marked, and drilling of the implant receiving cavity in the alveolar bone coiuences. The safe depth $D_{max}$ of an implant receiving cavity is calculated as explained herein above. Drilling is stopped a few millimeters $D_5$ (typically 1 or 2 mm) before reaching an estimated deepest physiologically safe implant receiving cavity.

While the invention has been described with respect to a limited number of embodiments, it will be appreciated that many variations, modifications and other applications of the invention can be made which still fall within the scope of the claims appended hereto.

What is claimed is:

1. An ultrasound system for use in assessment of an orthogonal distance between an area of interest (9;32) and a canal (12) extending within an alveolar bone (10) of either a subject's posterior mandible (8) or posterior maxilla, the system comprising:

(i) a single ultrasound probe (18) bringable into immediate physical contact with the area of interest (9;32) and capable of transceiving a pulse echo ultrasound signal to the alveolar bone (10) and therefrom; and (ii) an electronic circuitry (16) capable of processing the ultrasound signal and deriving therefrom the orthogonal distance (D1, $D_3$, $D_6$) between said ultrasound probe and the canal (12).

2. An ultrasound system according to claim 1, wherein the ultrasound probe (18) is placeable either immediately on the exposed alveolar bone (10) or on a soft tissue of an unexposed alveolar bone, and said electronic circuitry (16) is adapted to derive the orthogonal distance ($D_1$) by multiplying the time of flight ($T_{D1}, T_{D0}$) of the ultrasonic signal through the bone tissue or through the soft tissue by the average velocity ($V_{bone}, V_{soft}$) of propagation of the ultrasound signal through the bone tissue or the soft tissue.

3. An ultrasound system according to claim 1, wherein the area of interest is an implant receiving cavity (32) drilled in the alveolar bone (10), and where the ultrasound probe (18) is insertable into said cavity (32).

4. An ultrasound system according to claim 3, wherein said electronic circuitry (16) is adapted to derive the orthogonal distance ($D_3$) between the probe (18) and superior surface of the canal (12) by multiplying the time of flight ($T_{D3}$) of the ultrasonic signal by the actual velocity ($V_{boneact}$) of propagation of the ultrasound signal through the bone tissue between the implant receiving cavity (32) and the superior surface of the canal (12).

5. An ultrasound system according to claim 3, wherein the electronic circuitry (18) is adapted to provide an indication on arrival at a predetermined distance (D5) between canal (12) and a bottom of the implant receiving cavity (32), and said system comprises a display means (22) for displaying a graphic representation indicating the location of the probe (18) with respect to the canal (12).

6. An ultrasound system according to claim 1, wherein the probe (18) is positionable perpendicular with respect to a longitudinal axis of the canal (12).

7. An ultrasound system for use in assessment of the condition of an alveolar bone (10) of either a subject's posterior mandible (8) or posterior maxilla, in which a canal (12) extends, the system comprising:

(i) a single ultrasound probe (18) bringable into immediate physical contact with an area (9) of interest and transceiving pulse echo ultrasound signal immediate to the alveolar bone (10) and therefrom; and (ii) an electronic circuitry (16) capable of processing the ultrasound signal, and deriving therefrom an indication of the mechanical condition of the alveolar bone (10) at a portion of the bone (10) orthogonally extending between the ultrasound probe (18) and the canal (12).

8. A method for assessment of actual orthogonal distance ($D_{6act}$) between a bottom of an implant receiving cavity 32 and a canal (12) extending in an alveolar bone (10) of either a subject's posterior mandible (8) or posterior maxilla, the method comprising:

(i) drilling in the bone (10) the implant receiving cavity having known first depth ($D_2$);

(ii) based on the time of flight ($T_{D3}$) of an ultrasound signal propagation through the bone (10), accessing a distance ($D_3$) between the bottom of the cavity (32) and the canal (12);

(iii) increasing the depth ($D_2$) of the cavity (32) by a known distance ($D_4$);

(iv) based on the time of flight ($T_{D6}$) of the ultrasound signal propagating through the remaining part of the bone (10), assessing the new distance ($D_6$) between the bottom of the cavity (32) and the canal (12);

(v) calculating the actual velocity ($V_{boneact}$) of propagation of the ultrasound signal within said bone (10) according to the formula:

$$V_{boneact}=D_4/(T_{D3}-T_{D6})$$

(vi) calculating the actual orthogonal distance ($D_{6act}$) according to the formula:

$$D_{6act}=T_{D6}*V_{boneact}.$$

9. A method according to claim 8, including deriving a maximum safe drilling depth ($D_{max}$) of the implant receiving cavity (32) by the formula:

$$D_{max}=D_{6act}-D_S$$

where ($D_S$) is a minimum safety distance to be maintained between the bottom of the implant receiving cavity (32) and the superior surface of the canal (12).

10. A method according to claim 8, wherein the distance D is measured with an ultrasound system comprising:

(i) a single ultrasound probe (18) bringable into immediate physical contact with the area of interest (9;32) and capable of transceiving a pulse echo ultrasound signal to the alveolar bone (10) and therefrom; and (ii) and electronic circuitry (16) capable of processing the ultrasound signal and deriving therefrom the orthogonal distance ($D1$, $D_3$, $D_6$) between said ultrasound probe and the canal (12).

11. A method according to claim 8, wherein mechanical properties of the bone are estimated according to information derived out from $V_{boneact}$ and comparison to normal control values.

* * * * *